US008414636B2

United States Patent
Nabulsi et al.

(10) Patent No.: US 8,414,636 B2
(45) Date of Patent: Apr. 9, 2013

(54) INTRODUCER WITH RATCHET HANDLE DRIVE

(75) Inventors: Samih Nabulsi, Brisbane (AU); Swee Choong Ng, Sheung Wan (HK); Ben Cramp, Oxley (AU); Neil Davidson, Yeronga (AU); Craig Mounsey, Brisbane (AU); Cambell Smyth, Highgate Hill (AU); Chris Townsend, Gordon Park (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/467,337

(22) Filed: May 9, 2012

(65) Prior Publication Data

US 2012/0290066 A1 Nov. 15, 2012

(30) Foreign Application Priority Data

May 11, 2011 (AU) ................................ 2011202174

(51) Int. Cl.
*A61F 2/06* (2006.01)
(52) U.S. Cl. ..................................... 623/1.11; 623/1.12
(58) Field of Classification Search .................. 623/1.11, 623/1.12; 606/108, 200
See application file for complete search history.

(56) References Cited

U.S. PATENT DOCUMENTS

| 5,601,568 A | 2/1997 | Chevillon et al. |
| 5,618,300 A | 4/1997 | Marin et al. |
| 6,599,296 B1 * | 7/2003 | Gillick et al. ................. 606/108 |
| 2008/0208209 A1 | 8/2008 | Fischer et al. |

FOREIGN PATENT DOCUMENTS

| DE | 102005051469 A1 | 4/2007 |
| EP | 1964532 B1 | 12/2010 |
| WO | 9853761 | 12/1998 |
| WO | 0018330 A1 | 4/2000 |
| WO | 03101518 A1 | 12/2003 |

* cited by examiner

*Primary Examiner* — Julian Woo
(74) *Attorney, Agent, or Firm* — Richard J. Godlewski (57) ABSTRACT

A stent graft introducer has stent graft releasably retained onto a deployment catheter and a sheath encloses the stent graft. A handle assembly has a handle, a first slide and a second slide. The first slide retracts within the second slide and the second slide retracts within the handle. An actuation arrangement comprises a first longitudinal gear rack on the first slide, a second longitudinal gear rack on the second slide and a ratchet lever assembly on the handle. Actuation of the ratchet lever assembly causes the second slide to fully retract into the handle at which time the ratchet lever assembly engages the first gear rack through an aperture in the second rack and continued actuation causes retraction of the first slide thereby retracting the sheath from the pusher to expose the stent graft.

12 Claims, 6 Drawing Sheets

INTRODUCER WITH RATCHET HANDLE DRIVE

INCORPORATION BY REFERENCE

The following co-pending patent applications are referred to in the following description:
PCT Patent Publication No. WO 98/53761 entitled "A Prosthesis and a Method Deploying a Prosthesis"
PCT Publication WO 03/101518 entitled "Trigger Wire System for a Prosthesis Deployment Device"
The entire contents of these applications is hereby incorporated by reference.

FIELD OF INVENTION

This invention relates to a medical device and more particularly to a device for endovascular deployment of a stent graft.

BACKGROUND OF THE INVENTION

In our earlier patent application, PCT Patent Publication No. WO 98/53761 entitled "A Prosthesis and a Method Deploying a Prosthesis" there is disclosed an introducer for a stent graft which retains the stent graft so that each end can be moved and released independently during the process of endovascular deployment of the stent graft. This device requires that a number of actions be taken in a particular consecutive order to place a stent graft in the required position in the vasculature and then release one end of the stent graft and then another end and if required, between the release of each of the ends, the placement of a branch stent graft into a side arm of the stent graft. These features and other features disclosed in PCT Patent Publication No. WO 98/53761 are incorporated herewith in their entirety into this specification.

It is desirable that the set of sequential actions necessary to release the stent graft at the desired position in the vasculature be undertaken in the required order and that there be less chance for operator error during such a deployment.

It has been found, however, that a stent graft which includes self expanding stents engaging against the inner surface of the sheath, trigger wires retaining the graft onto the pusher as well as the general friction of interacting components can provide significant load. It is the intention of this invention to provide a system to assist with the withdrawing of a sliding portion into the handle of a delivery device.

It is the object of this invention therefore to provide a deployment device which is arranged to introduce, deploy and release a stent graft by a series of sequential actions.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

The invention will in general be discussed in relation to deployment of a stent graft into the abdominal aorta but the invention is not so limited and can apply to deployment into other portions of the aorta or into other vessels of the human or animal body.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

DESCRIPTION OF THE INVENTION

In one form the invention comprises a stent graft introducer comprising a deployment catheter and a handle assembly;
the deployment catheter comprising a pusher, a stent graft releasably retained onto the pusher, a temporary stent graft retention arrangement, a sheath coaxially around the pusher and enclosing the stent graft and a sheath hub to which the sheath is mounted;
the handle assembly comprising, a handle, a first slide and a second slide, the first slide able to slide to retract within the second slide and the second slide able to slide to retract within the handle, the first slide including a releasable engagement arrangement to engage and retain the sheath hub thereon, and an actuation arrangement to enable retraction of the second slide within the handle and the first slide within the second slide;
the handle being engaged with the pusher;
the actuation arrangement comprising a first longitudinal gear rack on the first slide, a second longitudinal gear rack on the second slide and a ratchet assembly on the handle, the ratchet assembly comprising a hand actuatable ratchet lever and an arm extending from the ratchet lever and engaging the second gear rack; whereby actuation of the hand actuatable ratchet lever causes the arm to engage gear teeth on the second gear rack to cause retraction of the second slide, the second slide comprising an aperture in the second gear rack whereby when the second slide is fully retracted into the handle, the arm extends through the aperture and engages the first gear rack and continued actuation of the hand actuatable ratchet lever causes the arm to engage gear teeth on the first gear rack to cause retraction of the first slide thereby retracting the sheath from the pusher to expose the stent graft retained on the pusher.

Preferably the ratchet assembly comprises a resilient arrangement to return the hand actuatable ratchet lever to an active position after it has been actuated. The resilient arrangement can comprise a spring or an integral hinge.

Preferably the hand actuatable ratchet lever comprises locked retracted position when the lever is adjacent to the handle.

Preferably the handle comprises an actuation and release arrangement for the temporary stent graft retention arrangement.

Preferably the handle comprises first and second trigger wire release mechanisms at a distal end thereof, the first and second trigger wire release mechanisms being connected to trigger wires which engage the sent graft to is temporarily retain the stent graft to the stent graft deployment device, the first and second trigger wire release mechanisms being movable to be disengaged from the distal end of the handle to pull the trigger wires to release the stent graft from the deployment catheter.

The first and second trigger wire release mechanisms can be engaged onto the distal end of the fixed portion by respective interengaging screw threads and the first and second trigger wire release mechanisms are movable to be disengaged from the distal end of the fixed portion by being rotated with respect to the fixed portion.

Preferably each of the first and second trigger wire release mechanisms comprise a rotating portion and a longitudinally moving portion, the longitudinally moving portion being engaged into a longitudinal track in the fixed portion and the interengaging screw thread being on the rotating portion and the trigger wires being affixed to the longitudinally moving portion.

Preferably the sheath hub is releasably engaged with the proximal end of the first slide.

Preferably the releasable engagement of the sheath hub with the proximal end of the first slide comprises a hub shroud around the hub and a locking ring, the locking ring engaging the hub shroud and incorporating a bayonet interconnection with the proximal end of the second part, whereby rotation of the locking ring disengages the bayonet interconnection with the proximal end of the second part such that the hub shroud and locking ring can be removed from the proximal end of the second part.

BRIEF DESCRIPTION OF THE DRAWINGS

This then generally describes the invention but to assist with understanding reference will now be made to the accompanying drawings which show preferred embodiments of the invention.

In the drawings.

DESCRIPTION OF PREFERRED EMBODIMENT

Figure 1A:
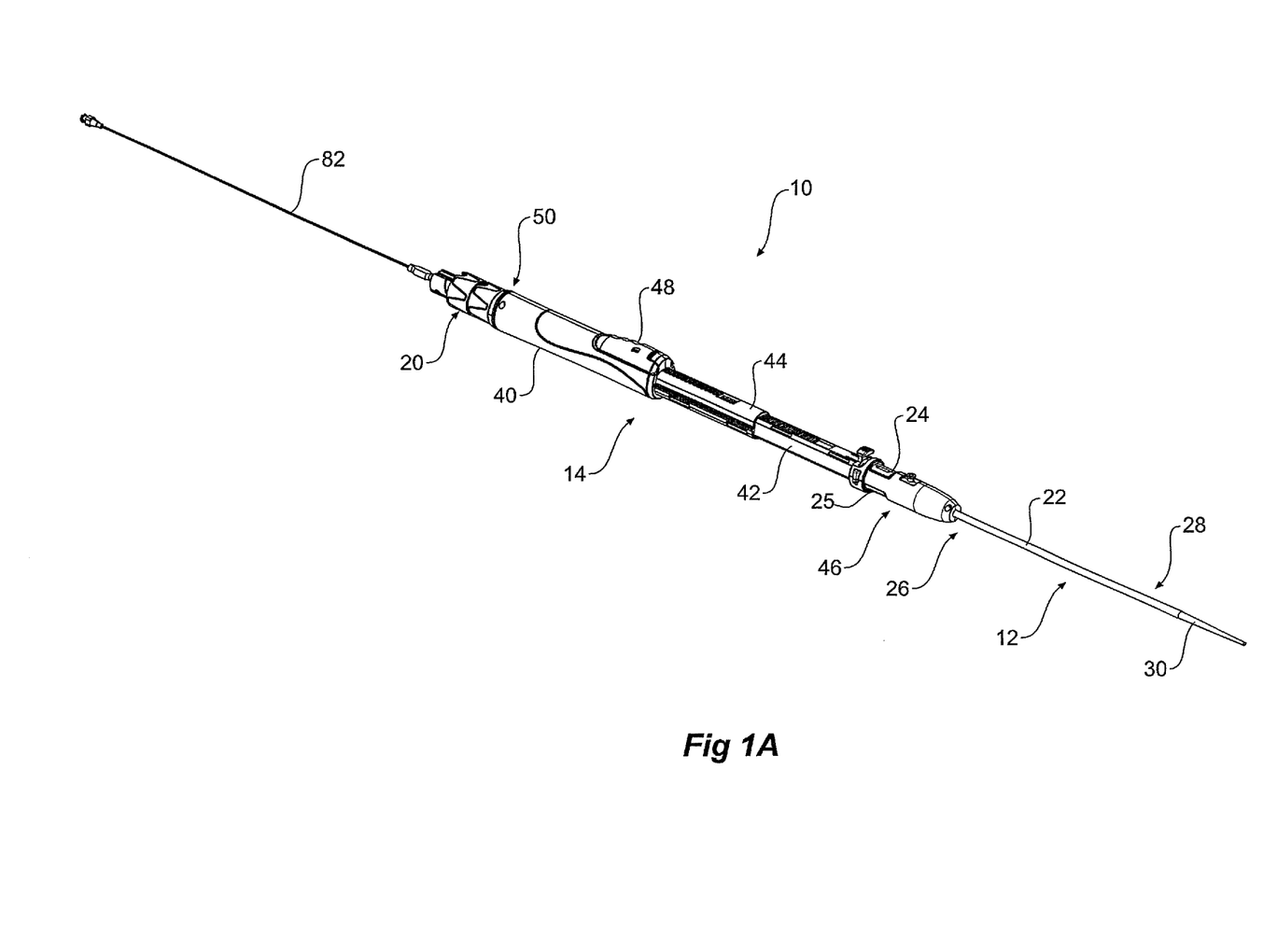
FIGS. 1A and 1B show perspective views of an embodiment of a endovascular delivery device according to the present invention.
Figure 1B:
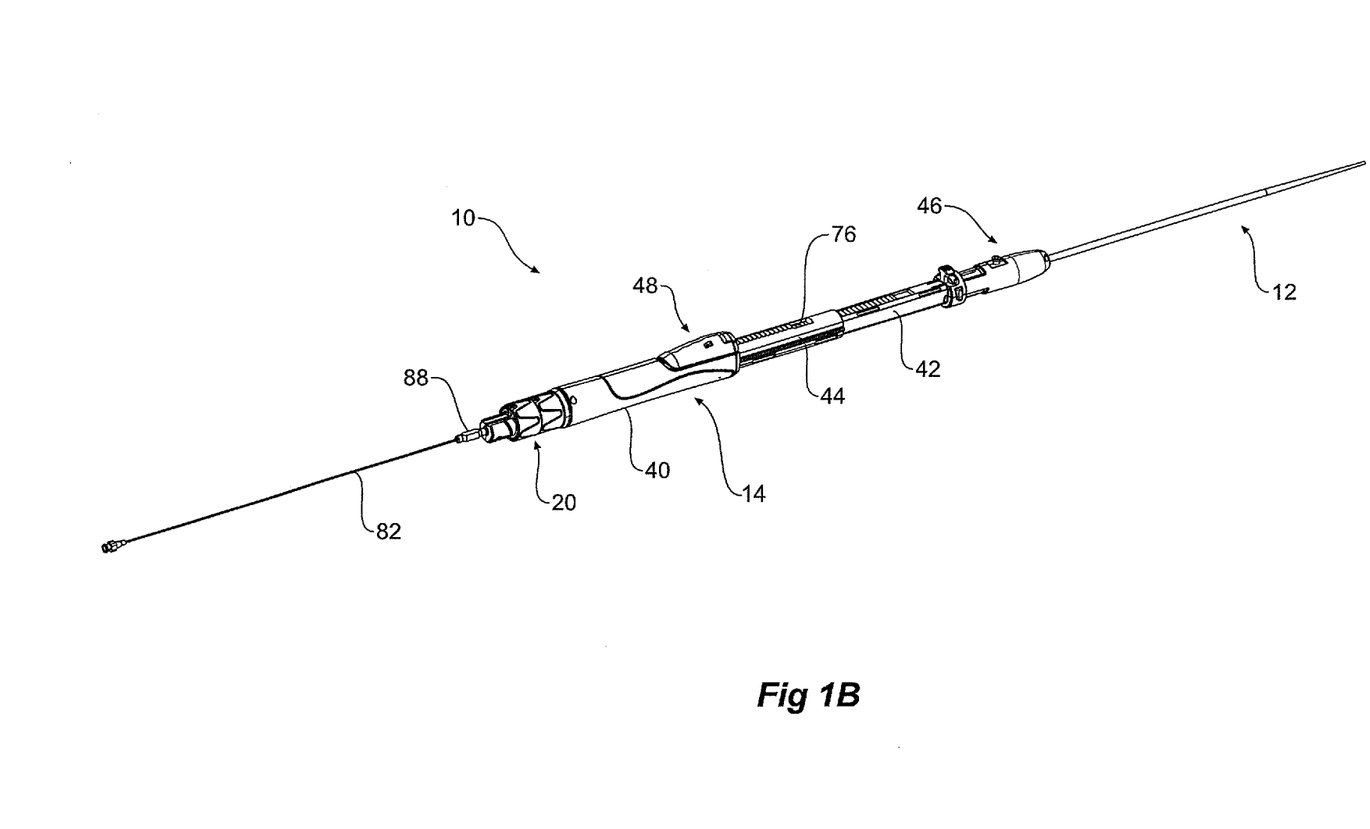

The endovascular delivery device according to one embodiment of the present invention shown in perspective in FIGS. 1A and 1B and various portions are shown in detail in FIGS. 2 to 6.

The endovascular delivery device 10 comprises a deployment catheter 12 and a handle assembly 14. The deployment catheter comprises a pusher 16, a stent graft releasably 18 retained onto the pusher and a temporary stent graft retention arrangement (not shown) and release arrangement 20 for the temporary stent graft retention arrangement on the handle assembly 14 as will be discussed in more detail below in relation to FIG. 6. A sheath 22 is coaxially around the pusher and encloses the stent graft (see in particular FIG. 3). A sheath hub 24 to which the sheath is mounted is at the distal end 26 of the sheath 22 and the sheath extends to a proximal end 28 where it engages around a nose cone dilator 30. The nose cone dilator 30, the sheath 22 and the pusher 16 are used to introduce the stent graft into the vasculature of a patient using the Seldinger technique. Once in place the sheath is retracted and the stent graft is released.

The sheath hub 24 can be a haemostatic valve such as a Captor Valve, Cook Inc, Bloomington, Ind., USA.

Patent application, PCT Patent Publication No. WO 98/53761 entitled "A Prosthesis and a Method Deploying a Prosthesis" discloses an introducer for a stent graft which retains the stent graft so that each end can be moved and released independently during the process of endovascular deployment of the stent graft and the teachings therein are incorporated herein in their entirety.

The handle assembly 14 comprises, a handle 40, a first slide 42 and a second slide 44. The first slide 42 is able to slide to retract within the second slide 44 and the second slide 44 is able to slide to retract within the handle 40. The first slide has a releasable engagement 46 to engage and retain the sheath hub thereon as will be discussing in more detail with respect to FIG. 6.

There is a particular advantage in having a handle, first slide that is able to slide to retract within the second slide and the second slide 44 that able to slide to retract within the handle. This means that for a relatively short handle a longer distance of retraction is possible because it is done in two stages. A stent graft may be up to 150 mm long so that for complete retraction of a sheath from such a stent graft at least 150 mm of retraction is needed. As the sheath initially extends beyond the retained stent graft to the nose cone dilator and must be retracted back onto the pusher at the distal end of the stent graft, up to 175 mm of retraction may be needed. All of this in one stage would mean that the handle would be very long. In two stages the length of each portion can be considerably less, making the device easier to handle.

The pusher 16 passes through first slide 42, the second slide 44 and handle 40 and the pusher is engaged with the handle 40 towards the distal end 50 of the handle at 52.

There is an actuation arrangement 48 on the handle 40 to enable retraction of the second slide 44 within the handle and the first slide 42 within the second slide 44. The actuation arrangement 48 comprises a first longitudinal gear rack 56 on the first slide 42, a second longitudinal gear rack 54 on the second slide 44 and a ratchet and pawl assembly 58 on the handle 40 which engages with the respective racks. The ratchet and pawl assembly 58 has a hand actuatable ratchet lever 60 and an arm 62 extending from the ratchet lever 60, the arm having a pawl 61 engaging the second gear rack 54. The hand actuatable ratchet lever 60 is pivoted to the handle on a transverse axis 64 and the arm 62 is pivoted to the hand actuatable ratchet lever 60 on a transverse axis 66. A torsion spring 70 acts between the hand actuatable ratchet lever 60 and the arm 62 to urge the arm away from the ratchet lever.

Figure 2:
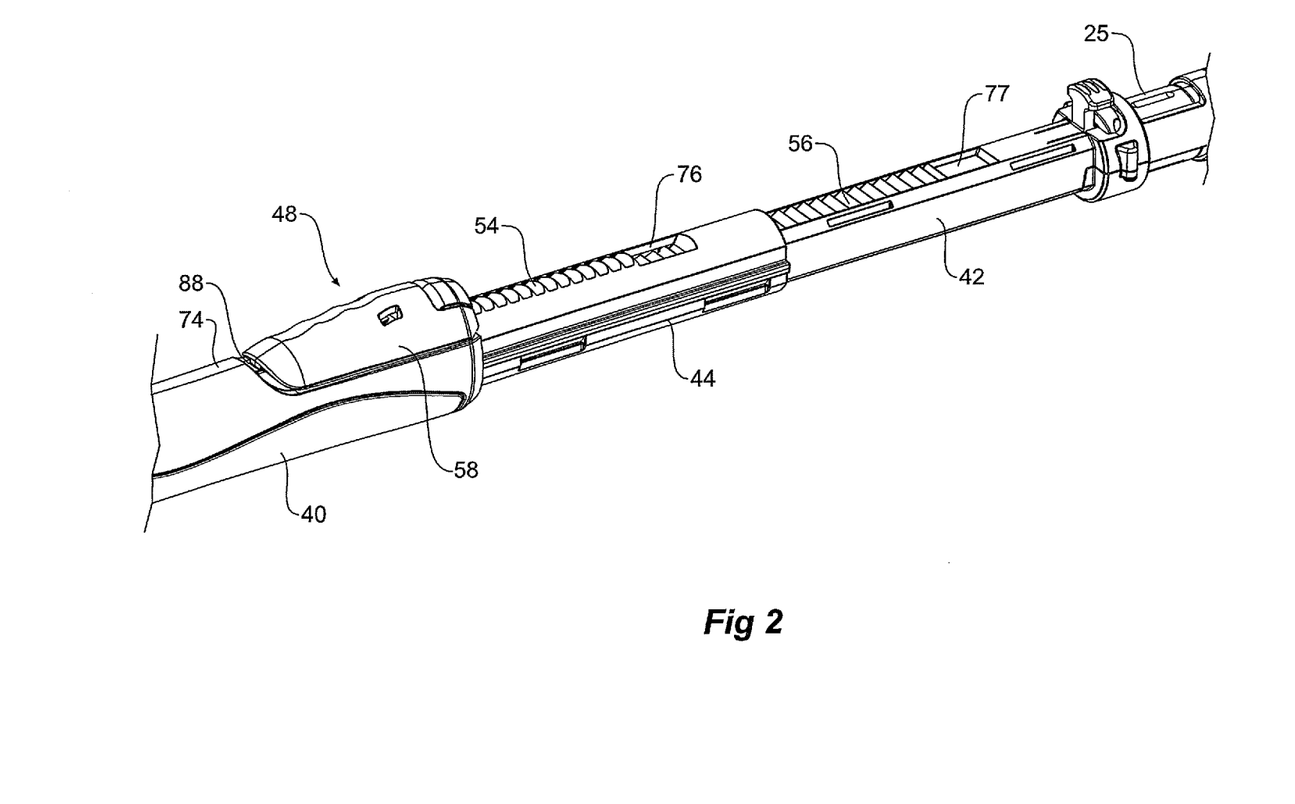
FIG. 2 shows detail of the actuation portion of the device of FIG. 1.
Figure 3:
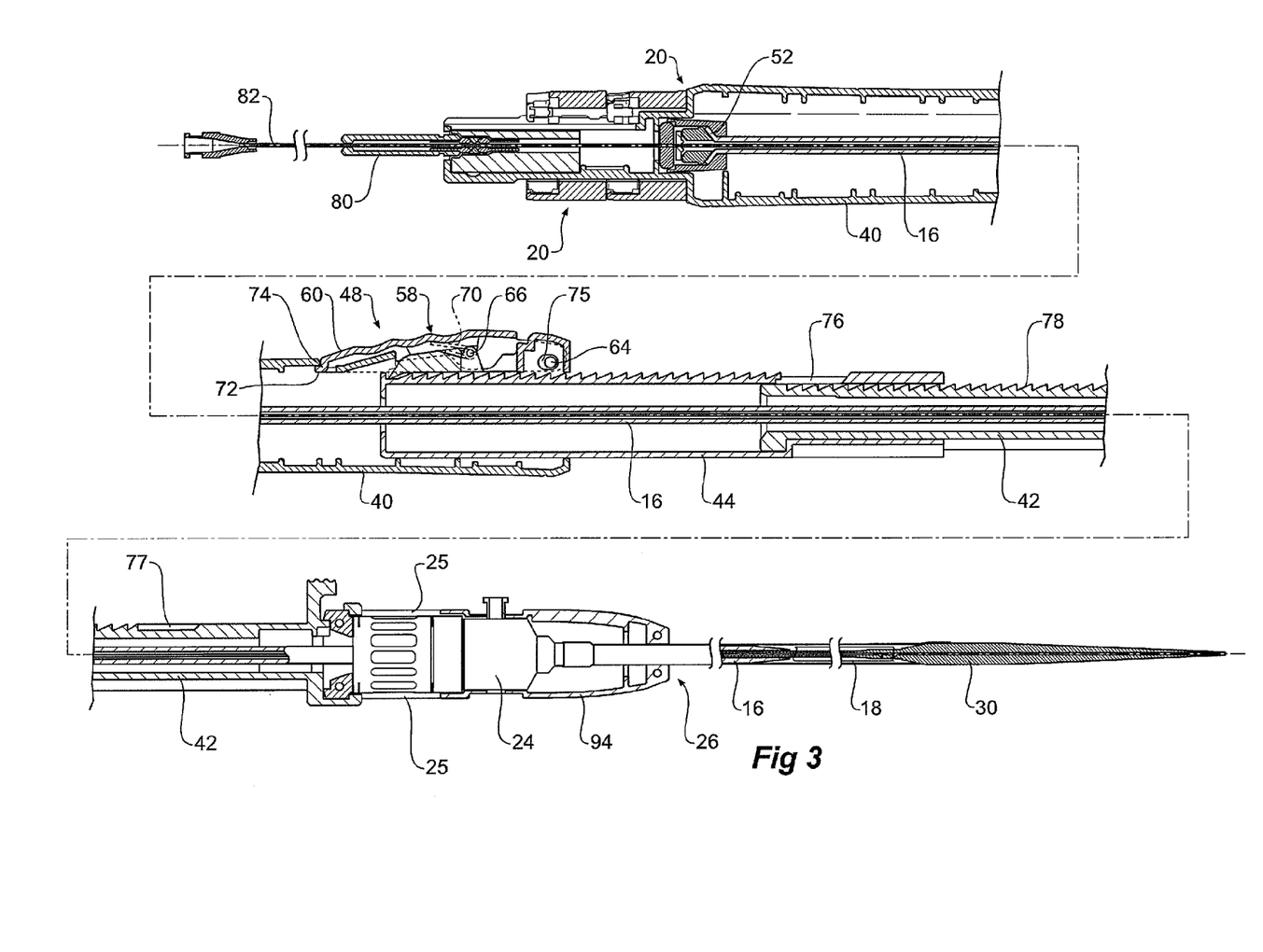
FIG. 3 shows a cross sectional view of the embodiment shown in FIG. 1A and 1B.
Figure 4:
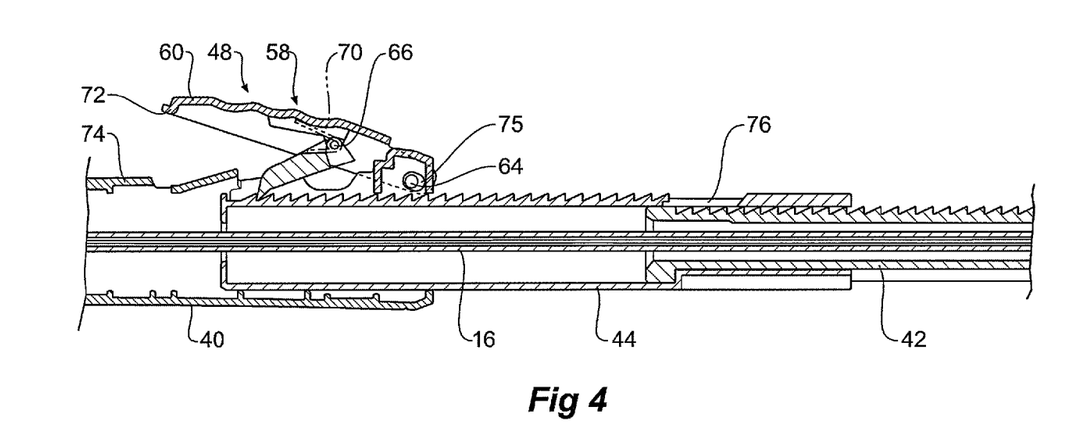
FIG. 4 shows part of the embodiment of FIG. 3 but with actuation lever released from its stowed position.
Figure 4A:
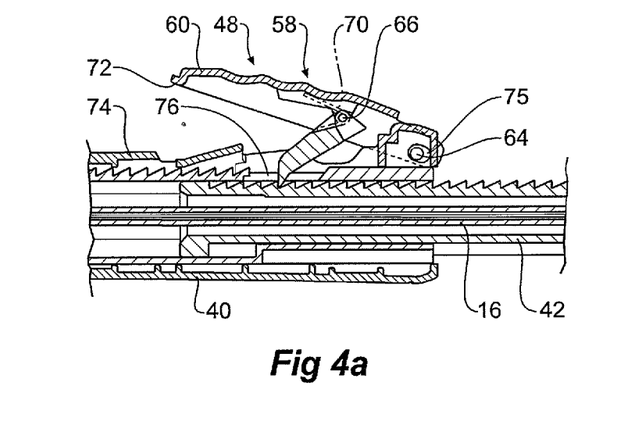
FIG. 4A shows the second slide fully retracted and the lever acting on the first slide when the ratchet lever is engaged with the inner rack through the aperture in the outer rack.

The hand actuatable ratchet lever 60 has a tongue 72 which, when the lever 60 is depressed and moved distally can engage under a ledge 74 on the handle 40 to enable the lever 60 to stay in a retracted configuration. For this purpose the lever has an oblong recess 75 through which the axis 64 extends thereby enabling the lever to be moved proximally and distally when the lever is in a retracted position as shown in FIG. 2 for instance as well as being able to be rotated around the axis 64. When the lever 60 is moved proximally the tongue 72 disengages from the ledge 74 and the spring 70 causes the lever 60 to move into its actuation condition as discussed below.

Actuation of the hand actuatable ratchet lever 60 causes the pawl 61 on the arm 62 to engage gear teeth 72 on the second gear rack 54. Depression of the lever 60 against the loading of the spring 70 causes the arm 62 to engage is gear teeth 72 and push in a distal direction and hence the second slide is moved in a distal direction. As the second slide 44 is engaged with the first slide 42 and first slide 42 is engaged with the sheath hub 24 the actuation of the lever causes the sheath hub 24 and hence the sheath 22 to be retracted or moved in a distal direction away from the nose cone dilator 30 which in turn exposes the stent graft 18. Release and re-actuation of the lever 60 causes the first slide to continue moving distally.

Continued actuation of the lever with the arm 62 engaging the gear teeth 72 on the second gear rack 54 can continue until the second slide has moved to the extent that an aperture 76 at the proximal end of the second rack 54 is reached. At this stage the second slide is fully retracted into the handle 40. The arm 62 and pawl 61 then extends through the aperture 76 and the pawl 61 engages gear teeth 78 on the second gear rack 56. Continued actuation of the lever 60 with the pawl 61 engaging the gear teeth 78 on the first gear rack 55 can continue until the first slide 42 is fully retracted into the second slide 44. This stage is particularly shown in FIG. 4A.

A recess 77 at the proximal end of the first rack 56 prevents further retraction of the first slide once the pawl reaches the recess 77.

By this time the sheath 22 is fully retracted and the stent graft 18 is fully exposed. During the retraction the movement can be stopped at any time to check the position of the stent graft in the vasculature of the patient and to reposition the delivery device as necessary. In some circumstances once the stent graft has been partially exposed a proximal retention arrangement may be released, as discussed below, to finally position the proximal end of the stent graft. Subsequently, the retraction of the sheath may be completed and the distal end of the stent graft correctly positioned before the distal end of the stent graft is released as discussed below.

Once both the proximal and distal retention arrangements have been released the introduction device can be withdrawn from the patient in its entirety or the sheath can be left in place for further procedures and the rest of the device removed.

For the former, the nose cone dilator 30 has first to be withdrawn back to the sheath and to do this a pin vice 80 which fixes a guide wire cannula 82, which extends through the pusher to and fastened to the nose cone dilator, with respect to the pusher, is released to enables the nose cone dilator 30 to be withdrawn to the sheath and then the entire device can be removed.

For the latter action, the nose cone dilator 30 has first to be withdrawn back to the sheath as discussed above and then the sheath hub must be released from the proximal end of the first slide. This action is discussed below with reference to FIG. 6. The hub can then be held and the handle assembly 14 withdrawn from it which withdraws, in turn, the pusher 16, the guide wire cannula 82 and the nose cone dilator 30.

Figure 5:
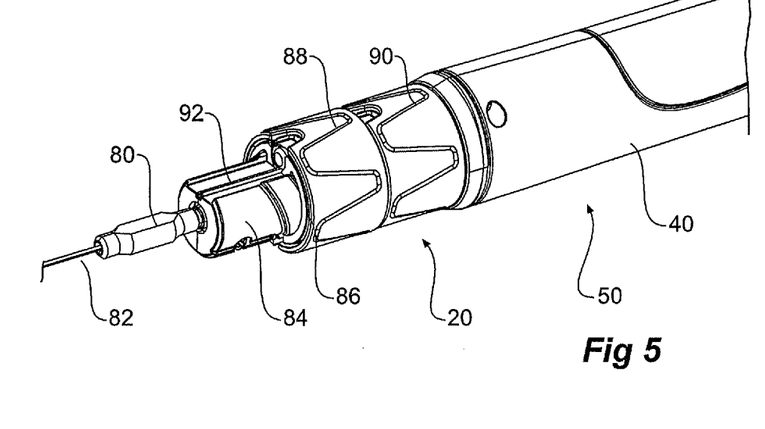
FIG. 5 shows detail of the trigger wire release portion of the endovascular delivery device according to the present invention.

FIG. 5 shows detail of the distal end of the handle 40 and the release arrangement 20 for the temporary stent graft retention arrangement.

The stent graft is retained at its proximal and distal ends to the nose cone dilator and pusher, respectively, by trigger wires which engage with the stent graft and extend back through the pusher to the of the distal end of the handle 40 and the release arrangement 20 for the temporary stent graft retention arrangement.

PCT Publication WO 03/101518 entitled "Trigger Wire System for a Prosthesis Deployment Device" discloses stent graft retention systems and the teachings therein are incorporated herein in their entirety.

At the distal end of the handle 40 there is a cylindrical portion 84 and this has a screw thread 86 on its outer surface. Two trigger wire release rings 88 and 90 are mounted on the cylindrical portion 84 and have an internal screw thread which engages into the screw thread 86. Rotation of the two trigger wire release rings 88 and 90 causes retraction of the respective trigger wires and hence release of the respective part of the stent graft. Each release ring 88 and 90 has a rotating part and a longitudinally moving part. The longitudinally moving part has a tongue which engages into a track 92 on the cylindrical portion 84 and this tongue allows transfer of rotation of the rotating part to longitudinal movement of the longitudinally moving part. The rotating part can rotate with respect to the longitudinally moving part. Trigger wires for release of the stent graft (not shown) are fastened to the part longitudinally moving part so that rotation of the rotating part causes longitudinal movement of the longitudinally moving part which in turn pulls the respective trigger wire.

Usually the release arrangement is such that the more distal release ring 88 is connected to the trigger wire which retains the proximal end of the stent graft and the more proximal release ring 90 is connected to the trigger wire which retains the distal end of the stent graft. As the release ring 88 must be moved first this means that the proximal end of the stent graft is usually released first.

Figure 6:
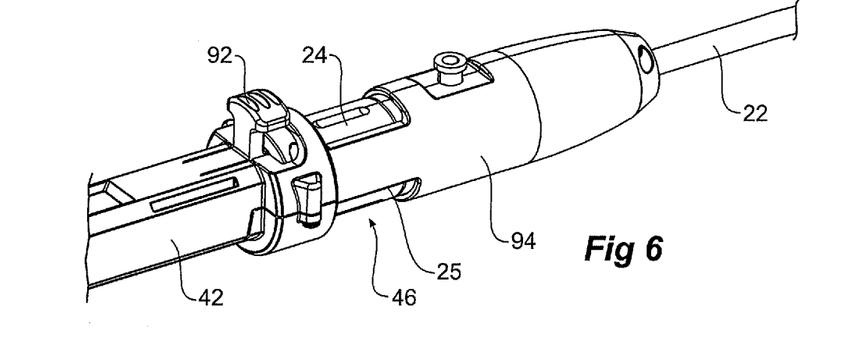
FIG. 6 shows detail of the sheath hub retention and release mechanism portion of the endovascular delivery device according to the present invention.

FIG. 6 shows detail of the housing 46 for the sheath hub 24 and sheath 22.

The sheath 22 has a hub assembly 24 at its distal end and the hub assembly is received in a releasable housing 46 at the proximal end of the first slide 42. The releasable housing 46 comprises a socket 94 into which the hub 24 is received and there is a releasable engagement of the socket to the proximal end of the first slide with a bayonet type engagement. Movement of the bayonet type fitting from an engaged to a disengaged position is restricted by a button 92. The releasable housing 46 has openings 25 through which the haemostatic valve of the hub 24 can be operated.

Depression of the button 92 enables the socket 94 to be rotated enough to remove it from the bayonet fitting and be released from the proximal end of the first slide 42. The socket stays with the hub 24 while the handle assembly 14 can be withdrawn from it, which withdraws, in turn, the pusher 16, the guide wire cannula 82 and the nose cone dilator 30.

In the case of a problem during deployment of a stent graft in which it is desirable to more manually operate the delivery device the button 92 can be depressed and the socket released to enable removal of the hub. At the same time the various components of the handle assembly can be dismantled.

Figure 7:
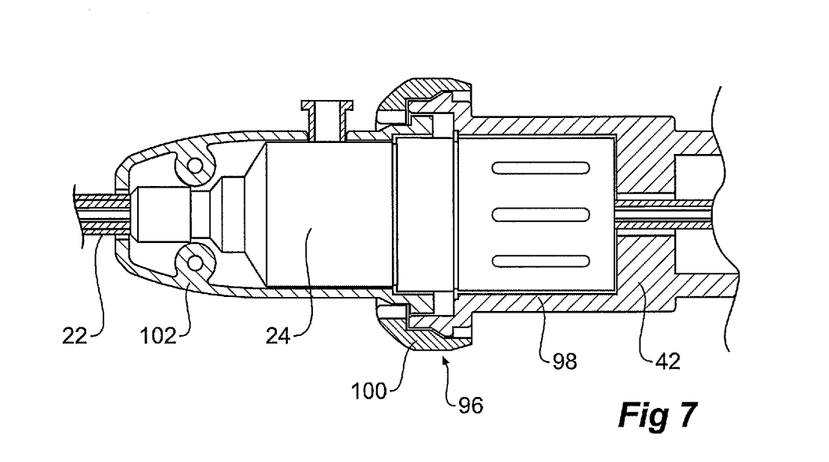
FIG. 7 shows detail of an alternative sheath hub retention and release mechanism portion of the endovascular delivery device according to the present invention.

FIG. 7 shows detail of an alternative sheath hub retention and release mechanism portion of the endovascular delivery device according to the present invention. The sheath 22 has a hub assembly 24 at its distal end and the hub assembly is received in a releasable housing 96 at the proximal end of the first slide 42. The releasable housing 96 comprises a socket 98 into which the hub 24 is received and a bayonet fitted locking nut 100 engages against the releasable housing 96 and holds a forward part 102 of the housing against the housing and capturing the hub 24.

In the case of a problem during deployment of a stent graft in which it is desirable to more manually operate the delivery device the nut 100 can be released to enable removal of the hub. At the same time the various components of the handle can be dismantled.

What is claimed is:

1. A stent graft introducer comprising a deployment catheter and a handle assembly;
   the deployment catheter comprising a pusher, a stent graft releasably retained onto the pusher, a temporary stent graft retention arrangement, a sheath coaxially around the pusher and enclosing the stent graft and a sheath hub to which the sheath is mounted;
   the handle assembly comprising, a handle, a first slide and a second slide, the first slide able to slide to retract within the second slide and the second slide able to slide to retract within the handle, the first slide including a releasable engagement arrangement to engage and retain the sheath hub thereon, and an actuation arrangement to enable retraction of the second slide within the handle and the first slide within the second slide;

the handle being engaged with the pusher;

the actuation arrangement comprising a first longitudinal gear rack on the first slide, a second longitudinal gear rack on the second slide and a ratchet and pawl assembly on the handle, the ratchet and pawl assembly comprising a hand actuatable ratchet lever and an arm extending from the ratchet lever and engaging the second gear rack; whereby actuation of the hand actuatable ratchet lever causes the arm to engage gear teeth on the second gear rack to cause retraction of the second slide, the second slide comprising an aperture in the second gear rack whereby when the second slide is fully retracted into the handle, the arm extends through the aperture and engages the first gear rack and continued actuation of the hand actuatable ratchet lever causes the arm to engage gear teeth on the first gear rack to cause retraction of the first slide thereby retracting the sheath from the pusher to expose the stent graft retained on the pusher.

2. A stent graft introducer as in claim 1 wherein the ratchet assembly comprises a resilient arrangement to return the hand actuatable ratchet lever to an active position after it has been actuated.

3. A stent graft introducer as in claim 1 wherein the resilient arrangement comprises a spring.

4. A stent graft introducer as in claim 1 wherein the resilient arrangement comprises an integral hinge.

5. A stent graft introducer as in claim 1 wherein the hand actuatable ratchet lever comprises locked retracted position when the lever is adjacent to the handle.

6. A stent graft introducer as in claim 1 wherein the handle comprises an actuation and release arrangement for the temporary stent graft retention arrangement.

7. A stent graft introducer as in claim 1 wherein the handle comprises first and second trigger wire release mechanisms at a distal end thereof, the first and second trigger wire release mechanisms being connected to trigger wires which engage the stent graft to temporarily retain the stent graft to the stent graft deployment device, the first and second trigger wire release mechanisms being movable to be disengaged from the distal end of the handle to pull the trigger wires to release the stent graft from the deployment catheter.

8. A stent graft introducer as in claim 7 wherein the first and second trigger wire release mechanisms are engaged onto the distal end of the handle by respective interengaging screw threads and the first and second trigger wire release mechanisms are movable to be disengaged from the distal end of the fixed portion by being rotated with respect to the fixed portion.

9. A stent graft introducer as in claim 8 wherein each of the first and second trigger wire release mechanisms comprise a rotating portion and a longitudinally moving portion, the longitudinally moving portion being engaged into a longitudinal track in the handle and the interengaging screw thread being on the rotating portion and the trigger wires being affixed to the longitudinally moving portion.

10. A stent graft introducer as in claim 1 wherein the sheath hub is releasably engaged with a proximal end of the first slide.

11. A stent graft introducer as in claim 10 wherein the releasable engagement of the sheath hub with the proximal end of the first slide comprises a hub shroud around the hub and a locking ring, the locking ring engaging the hub shroud and incorporating a bayonet interconnection with the proximal end of the first slide, whereby rotation of the locking ring disengages the bayonet interconnection with the proximal end of the first slide such that the hub shroud and locking ring can be removed from the proximal end of the first slide.

12. A stent graft introducer comprising a deployment catheter and a handle assembly;

the deployment catheter comprising a pusher, a stent graft releasably retained onto the pusher, a temporary stent graft retention arrangement, a sheath coaxially around the pusher and enclosing the stent graft and a sheath hub to which the sheath is mounted;

the handle assembly comprising, a handle, a first slide and a second slide, the first slide able to slide to retract within the second slide and the second slide able to slide to retract within the handle, the first slide including a releasable engagement arrangement to engage and retain the sheath hub thereon, and an actuation arrangement to enable retraction of the second slide within the handle and the first slide within the second slide;

the handle being engaged with the pusher;

the actuation arrangement comprising a first longitudinal gear rack on the first slide, a second longitudinal gear rack on the second slide and a ratchet and pawl assembly on the handle, the ratchet and pawl assembly comprising a hand actuatable ratchet lever, an arm extending from the ratchet lever and engaging the second gear rack and a spring acting between the lever and the arm; whereby actuation of the hand actuatable ratchet lever causes the arm to engage gear teeth on the second gear rack to cause retraction of the second slide, the second slide comprising an aperture in the second gear rack whereby when the second slide is fully retracted into the handle, the arm extends through the aperture and engages the first gear rack and continued actuation of the hand actuatable ratchet lever causes the arm to engage gear teeth on the first gear rack to cause retraction of the first slide thereby retracting the sheath from the pusher to expose the stent graft retained on the pusher;

the handle comprising an actuation and release arrangement for the temporary stent graft retention arrangement; and the sheath hub being releasably engaged with a proximal end of the first slide.

* * * * *